US012324763B2

(12) United States Patent
Goldberg

(10) Patent No.: US 12,324,763 B2
(45) Date of Patent: Jun. 10, 2025

(54) POST-SURGICAL COMPRESSION GARMENT

(71) Applicant: Paul Goldberg, Delray Beach, FL (US)

(72) Inventor: Paul Goldberg, Delray Beach, FL (US)

( * ) Notice: Subject to any disclaimer, the term of this patent is extended or adjusted under 35 U.S.C. 154(b) by 0 days.

(21) Appl. No.: 18/236,385

(22) Filed: Aug. 21, 2023

(65) Prior Publication Data

US 2024/0058151 A1    Feb. 22, 2024

Related U.S. Application Data

(60) Provisional application No. 63/474,512, filed on Aug. 19, 2022.

(51) Int. Cl.
*A61F 5/03*    (2006.01)

(52) U.S. Cl.
CPC ..................................... *A61F 5/03* (2013.01)

(58) Field of Classification Search
CPC ...... A61F 5/03; A61F 5/05808; A61F 5/3746; A61F 2007/0001; A61F 2007/0018; A61F 2007/0022; A61F 2007/0023; A61F 2007/0024; A61F 2007/0025; A61F 2007/0026; A61F 2007/0027; A61F 2007/004; A61F 2013/00493
See application file for complete search history.

(56) References Cited

U.S. PATENT DOCUMENTS

| | | | | |
|---|---|---|---|---|
| 3,357,435 A | * | 12/1967 | Enrico | A41C 1/10 D2/714 |
| 8,784,347 B1 | * | 7/2014 | Smith | A61F 5/03 602/61 |
| 10,278,431 B2 | * | 5/2019 | McClean | A41D 1/14 |
| 2001/0037076 A1 | * | 11/2001 | Shelton | A41D 13/0058 602/5 |
| 2008/0256675 A1 | * | 10/2008 | Di Lorenzo | A41D 7/00 2/67 |
| 2013/0253397 A1 | * | 9/2013 | Samoodi | A41C 1/10 602/19 |

FOREIGN PATENT DOCUMENTS

| | | | |
|---|---|---|---|
| CN | 216776143 U | * | 6/2022 |
| JP | 2000096309 A | * | 4/2000 |

* cited by examiner

*Primary Examiner* — Tarla R Patel
(74) *Attorney, Agent, or Firm* — Mark C. Johnson; Johnson |Dalal

(57) ABSTRACT

A unitary garment body having a front abdominal portion interposed between two arm openings and the two leg openings of the garment, of an elastic-based polymer material, with an inner surface, defining at least one pocket interposed between outer and inner surfaces of the front abdominal portion and configured to enclose and define a pocket cavity shaped and sized to receive a thermal pack, and with a plurality of front pressure protrusions on the pocket and each projecting inwardly from the inner surface toward the abdomen cavity, disposed in a tightly spaced configuration, each having a rounded tip, and each having a width ranging from 1-2 mm and a height relative to the inner surface of the front abdominal portion ranging from 0.2-0.5 mm and having a rear back portion interposed also of an elastic-based polymer material opposing the front abdominal portion.

18 Claims, 4 Drawing Sheets

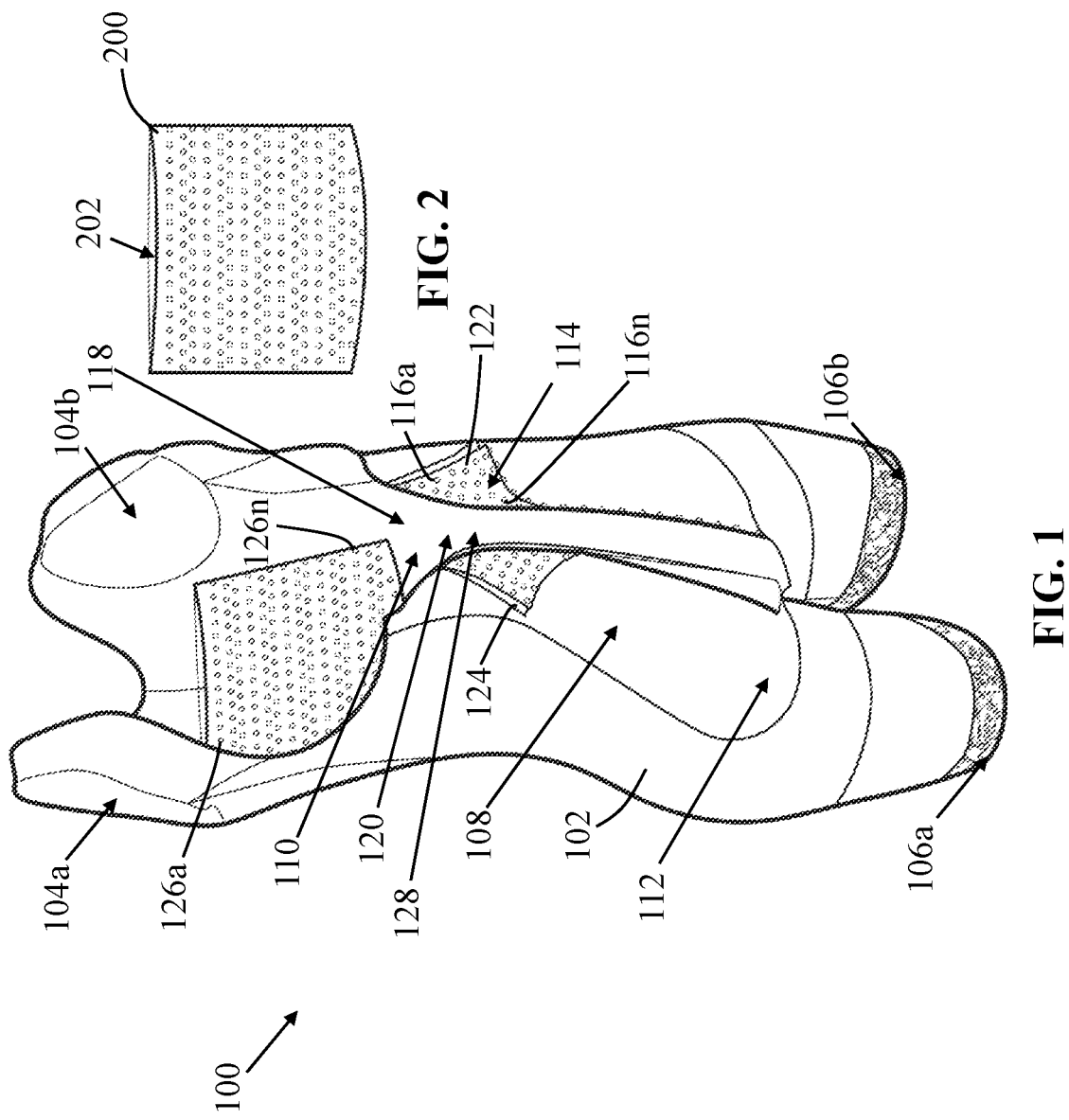

POST-SURGICAL COMPRESSION GARMENT

FIELD OF THE INVENTION

The present invention relates generally to compression garments and, more particularly, relates to compression garments applying targeted pressure and cooling for post-surgical purposes.

BACKGROUND OF THE INVENTION

Compression garments are very well known and generally provide a tight or snug fit to a user's body. These garments may be made from a variety of elastic materials, including nylon, spandex, or a silicon base. Many in the medical profession also utilize compression garments in the aid of post-performance recovery or for therapeutic use. These medical compression garments differ from other compression garments, e.g., for fitness use, in that they typically have more graduated compression along a length of the garment, are typically lighter in weight, typically have a higher-pressure range, e.g., 8- and 50-mmHg compared to 15- to 30-mmHG. These medical compression garments have been shown to decrease swelling, increase blood flow and circulation, aid in muscle recovery, reduce the likelihood of blood clotting, etc.

Some known medical compression garments utilize straps and rigid ribs to apply pressure to a patient, but they have often been found to be effective after repeated usage or when the patient moves significantly. Some known garments also utilize "dots" and other protrusions to apply pressure to the user's body, but they too are not of a conducive material and are not shaped and sized to be completely effective, particular in the context of post-surgical recovery, as they are generally utilized for muscle recovery.

Therefore, a need exists to overcome the problems with the prior art as discussed above.

SUMMARY OF THE INVENTION

The invention provides a post-surgical compression garment that overcomes the hereinafore-mentioned disadvantages of the heretofore-known devices and methods of this general type and that can be utilized for surgical and non-surgical applications, but beneficially includes an array of specially configured and sized elastic protrusions and pockets to receive a thermal pack.

With the foregoing and other objects in view, there is provided, in accordance with the invention, a post-surgical compression garment with a unitary garment body defining two arm openings, two leg openings, an abdomen cavity, and a body length separating an upper terminal edge of the unitary garment body and a lower terminal edge of the unitary garment body. The unitary garment body also has a front abdominal portion interposed between the two arm openings and the two leg openings, of an elastic-based polymer material, with an outer surface, with an inner surface opposing the outer surface of the front abdominal portion, defining at least one pocket interposed between the outer and inner surfaces of the front abdominal portion and configured to enclose and define a pocket cavity shaped and sized to receive a thermal pack, and with a plurality of front pressure protrusions each projecting inwardly from the inner surface of the front abdominal portion having the at least one pocket and toward the abdomen cavity, disposed in a tightly spaced configuration with one another spanning along the body length, each having a rounded tip, and each having a width ranging from 1-2 mm and a height relative to the inner surface of the front abdominal portion ranging from 0.2-0.5 mm. Further, the unitary garment body also has a rear back portion opposing the front abdominal portion, interposed between the two arm openings and the two leg openings, of an elastic-based polymer material, with an outer surface, and with an inner surface opposing the outer surface of the rear abdominal portion.

In accordance with a further feature of the present invention, the elastic-based polymer material of the front and rear abdominal portions is of a polyamide and elastane material.

In accordance with an additional feature of the present invention, the elastic-based polymer material of the front and rear abdominal portions is approximately 80% polyamide and approximately 20% elastane.

In accordance with another feature, an embodiment of the present invention includes the front and rear abdominal portions each having an interior layer of approximately 80% polyamide and 20% elastane and including the inner surface of the respective front abdominal portion or the rear abdominal portion and an exterior layer coupled to the interior layer, of approximately 85% polyamide and 15% elastane, and including the outer surface of the respective front abdominal portion or the rear abdominal portion.

In accordance with a further feature of the present invention, the interior layer of the front abdominal portion defines the at least one pocket and includes the plurality of front pressure protrusions directly coupled thereto.

In accordance with yet another feature of the present invention, the plurality of front pressure protrusions are either of a glass-based material or a polymer-based material.

In accordance with another feature, an embodiment of the present invention includes the rear back portion having at least one pocket defined thereon and interposed between the outer and inner surfaces of the rear abdominal portion and configured to enclose and define a pocket cavity shaped and sized to receive a thermal pack, and with a plurality of rear pressure protrusions each projecting inwardly from the inner surface of the rear abdominal portion having the at least one pocket and toward the abdomen cavity, disposed in a tightly spaced configuration with one another spanning along the body length, each having a rounded tip, and each having a width ranging from 1-2 mm and a height relative to the inner surface of the front abdominal portion ranging from 0.2-0.5 mm.

In accordance with yet another feature, an embodiment of the present invention also includes the front and rear abdominal portions each having an interior layer of approximately 80% polyamide and 20% elastane and including the inner surface of the respective front or rear abdominal portion and an exterior layer coupled to the interior layer, of approximately 85% polyamide and 15% elastane, and including the outer surface of the respective front or rear abdominal portion.

In accordance with a further feature of the present invention, the interior layer of the front abdominal portion defines the at least one pocket and includes the plurality of front pressure protrusions directly coupled thereto and the interior layer of the rear abdominal portion defines the at least one pocket and includes the plurality of rear pressure protrusions directly coupled thereto.

In accordance with an exemplary feature of the present invention, the plurality of front pressure protrusions and the plurality of rear pressure protrusions are either of a glass-based material or a polymer-based material.

In accordance with an additional feature of the present invention, the plurality of front pressure protrusions and the plurality of rear pressure protrusions are of a thermally conductive material with a thermal conductivity greater than 0.5 (W/m·K).

In accordance with yet another feature, an embodiment of the present invention also includes the unitary garment body having an upper terminal edge formed with the front abdominal portion, a slit defined thereon and spanning from the upper terminal edge, and at least one fastener operably configured to open and close the slit.

In accordance with an additional feature of the present invention, the slit is centrally disposed on the front abdominal portion.

In accordance with another feature of the present invention, the plurality of front pressure protrusions span along the body length beginning proximal to the upper terminal edge formed with the front abdominal portion.

In accordance with a further feature of the present invention, the plurality of front pressure protrusions are disposed in the tightly spaced configuration with one another spanning at least 10% of the body length.

In accordance with an additional feature of the present invention, the plurality of front pressure protrusions are disposed in the tightly spaced configuration no greater than approximately 8 mm.

Also in accordance with the present invention, a post-surgical compression garment is disclosed that includes a unitary garment body defining two arm opening, two leg openings, an abdomen cavity, and a body length separating an upper terminal edge of the unitary garment body and a lower terminal edge of the unitary garment body or having a front abdominal portion interposed between the two arm openings and the two leg openings, of an elastic-based polymer material, with an outer surface, with an inner surface opposing the outer surface of the front abdominal portion, defining at least one pocket interposed between the outer and inner surfaces of the front abdominal portion and configured to enclose and define a pocket cavity shaped and sized to receive a thermal pack, and with a plurality of front pressure protrusions each projecting inwardly from the inner surface of the front abdominal portion having the at least one pocket and toward the abdomen cavity, disposed in a tightly spaced configuration with one another spanning along the body length, each having a rounded tip. The garment also includes a rear back portion opposing the front abdominal portion, interposed between the two arm openings and the two leg openings, of an elastic-based polymer material, with an outer surface, with an inner surface opposing the outer surface of the rear abdominal portion, defining at least one pocket interposed between the outer and inner surfaces of the rear abdominal portion and configured to enclose and define a pocket cavity shaped and sized to receive a thermal pack, and with a plurality of rear pressure protrusions each projecting inwardly from the inner surface of the rear abdominal portion having the at least one pocket and toward the abdomen cavity, disposed in a tightly spaced configuration with one another spanning along the body length, and each having a rounded tip.

Although the invention is illustrated and described herein as embodied in a post-surgical compression garment, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the garment or spanning to-and-from the upper and lower terminal ends of the garment.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 1 is a partially exploded and transparent perspective view of a post-surgical compression garment in accordance with one embodiment of the present invention;

FIG. 2 is a perspective view of a pocket formed on one or both of the front and rear abdominal portions of the post-surgical compression garment in accordance with one embodiment of the present invention;

DETAILED DESCRIPTION

Figure 4:
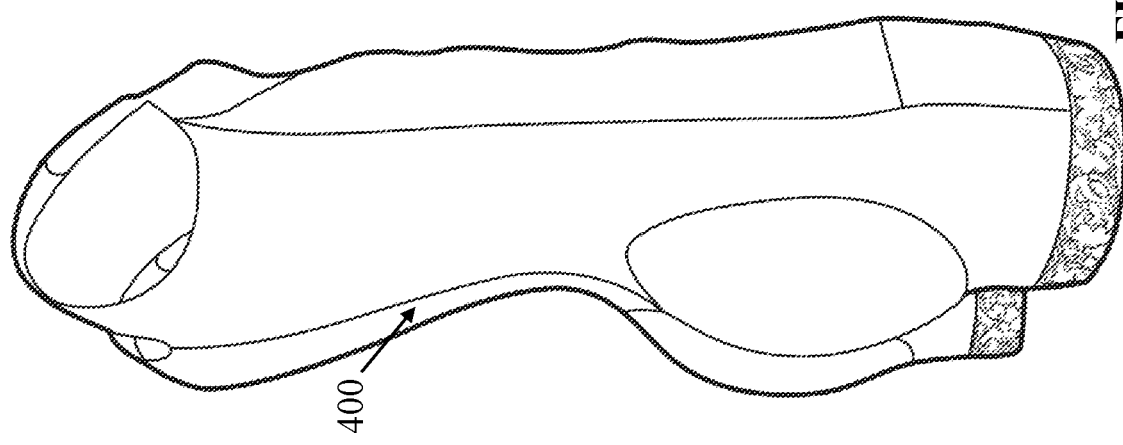
FIG. 4 is a perspective side view of the post-surgical compression garment in FIG. 1.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient post-surgical compression garment that effectively and safely facilitates in reducing post-surgical recovery time and otherwise has been demonstrated to more effectively decrease swelling, increase blood flow and circulation, aid in muscle recovery, and reduce the likelihood of blood clotting. To effectuate the same and with reference to FIG. 1, the post-surgical compression garment 100 includes specially configured and sized pressure protrusions 116a-n, 126a-n that may be disposed on the inner surfaces of both the front and rear portions of the garment 100 and may also include pockets for thermals packs, e.g., gel packs adjacent to said pressure protrusions 116a-n, 126a-n. Although FIG. 1 shows several advantageous features of the present invention, but, as will be described below, the invention can be provided in several shapes, sizes, combinations of features and components, and varying numbers and functions of the components.

Figure 3:
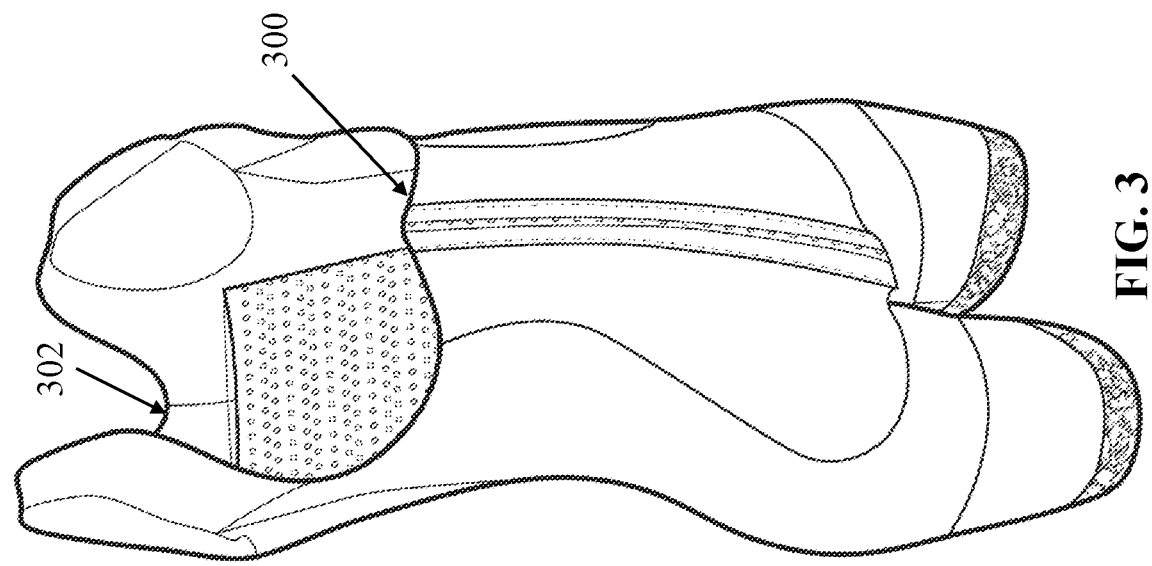
FIG. 3 is a perspective and partially transparent front view of the post-surgical compression garment in FIG. 1.
Figure 6:
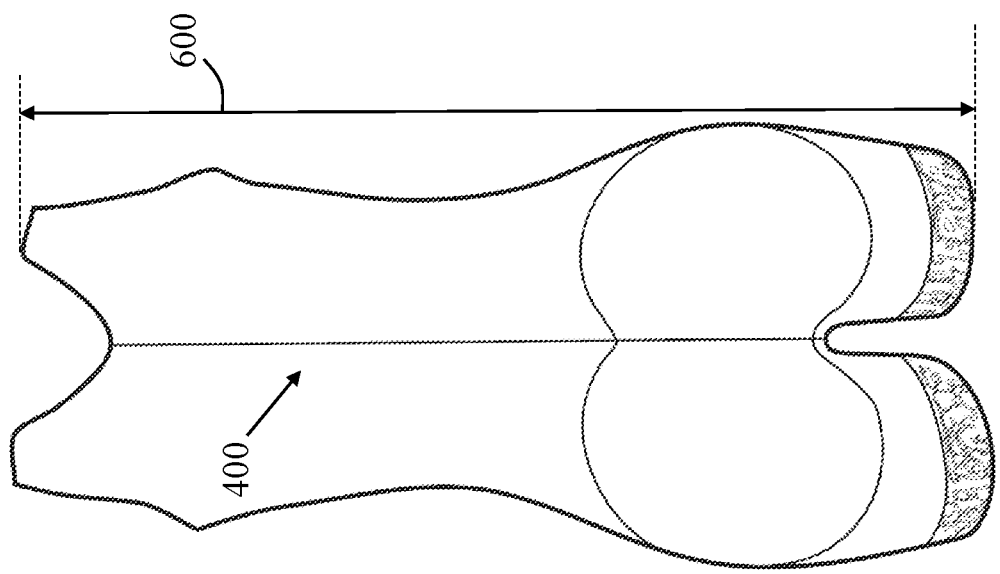
FIG. 6 is a rear elevational view of the post-surgical compression garment in FIG. 1.
Figure 5:
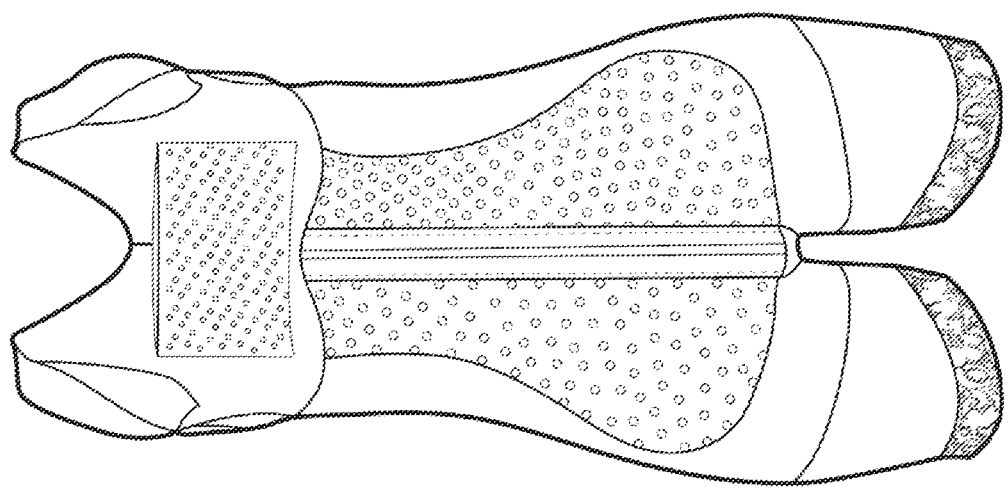
FIG. 5 is a front elevational view of the post-surgical compression garment in FIG. 1.

The first example of a post-surgical compression garment 100, as shown in FIG. 1, includes a unitary garment body 102 having a front abdominal portion 108 designed to cover and apply pressure to the anterior portion of the user's abdomen and a rear back portion 110 designed to cover and apply pressure to the posterior or back portion of the user's abdomen. The body is "unitary" in that it can be operated, moved, applied, worn, and taken off as one piece of material. Said another way, it has one or more components that are connected together to operate as a single unit. The front abdominal portion 108 opposes the rear abdominal portion 108 and each generally spans from a respective terminal edge 300, 302, respectively, to the inseam or seat of the garment 100 (best seen in FIG. 3). The garment 100 defines two arm openings 104a-n that may be enclosed, two leg openings 106a-b that may be enclosed, an abdomen cavity 118 that may be at least partially defined by the front an drear abdominal portions 108, 100, and a body length 600 (as best seen in FIG. 6) separating an upper terminal edge of the unitary garment body 102 and a lower terminal edge of the unitary garment body 102.

The two arm openings 104a-n and the two leg openings 106a-b are important and preferred has they prevent the garment 100 from becoming dislodged when in use. The abdomen cavity 118 opens at the top of the garment 100 where the user will insert his or her head and torso. The body length 600 may vary based on design constraints and user-design, but may range from 91-152 cm.

In one embodiment, the front and rear abdominal portions 108, 110 are interposed (at least partially or completely) between the two arm openings 104a-n and the two leg openings 106a-b, thereby enabling the garment 100 to apply pressure to the abdomen of the user. To that end, the front and rear abdominal portions 108, 110 are of an elastic-based polymer material. More specifically, the elastic-based polymer material of the front and rear abdominal portions 108, 110 is of a polyamide and elastane material, e.g., approximately (+/−10%) 80% polyamide, also commonly referred to as nylon, and approximately (+/−10%) 20% elastane. This material composition provides the requisite compression needed in the post-surgical recovery context.

Even more specifically, the front and rear abdominal portions 108, 110 also each include a layup made up of an interior layer (e.g., interior layer 122) that is of approximately 80% polyamide and 20% elastane and that includes the inner surface 114 of the respective front or rear abdominal portion. The layup also includes an exterior layer (e.g., exterior layer 124) that is coupled to the interior layer 122 using, for example, welding, adhesive, etc. The exterior layer 124 is preferably of approximately 85% polyamide and 15% elastane, thereby providing a multi-layered garment 100 that has been shown to more effectively provide recovery benefits in the context of post-surgical recovery. The exterior layer 124 also includes the outer surface 112 of the respective front or rear abdominal portion.

Figure 8:
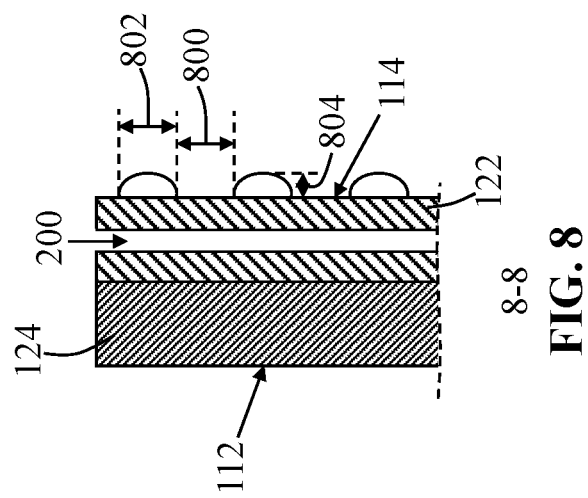
FIG. 8 is a close-up sectional view, along section 8-8 in FIG. 7, in accordance with one embodiment of the present invention.
Figure 7:
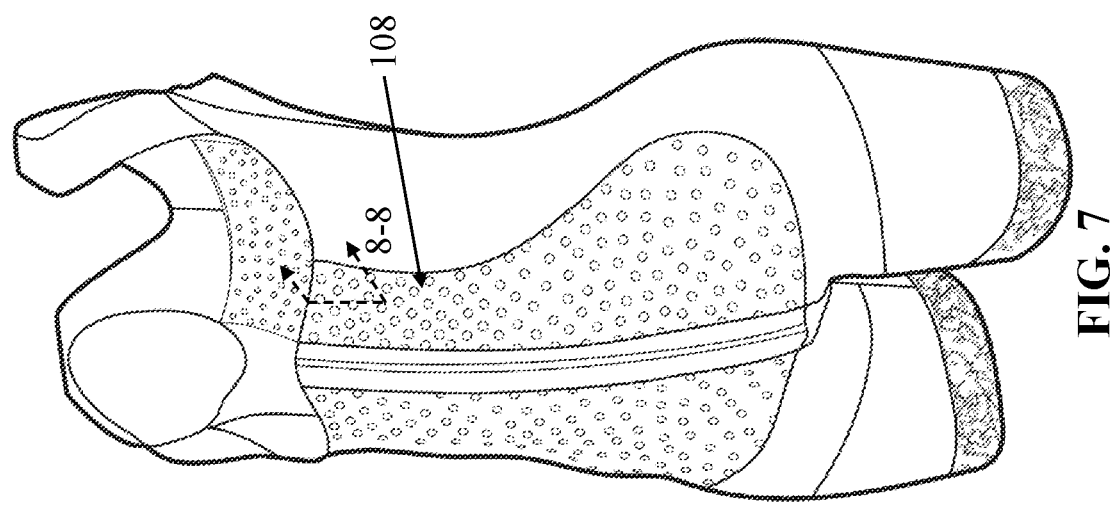
FIG. 7 is a front perspective and partially transparent view of the post-surgical compression garment in FIG. 1.

With reference to FIG. 2, FIG. 4, and FIG. 8 in combination with FIG. 1, the interior and exterior layers 122, 124 can be seen coupled to one another. Further, the front and/or rear abdominal portions 108, 110 can also be seen having outer surfaces 112, 400 and inner surfaces 114, 120 opposing the respective outer surfaces 112, 400. The front and/or rear abdominal portions 108, 110 may also beneficially include one or more pockets (see, e.g., pocket 200) interposed between the respective outer surfaces 112, 400 and inner surfaces 114, 120 of the respective front or rear abdominal portions 108, 110, wherein the pocket 200 is configured to enclose and define a pocket cavity shaped and sized to receive a thermal pack, e.g., a gel pack, wherein said limitation also includes a cooling tube. Said differently, the pocket 200 provides an enclosed portion of the garment 100 designed to selectively house and remove a thermal pack, preferably a flexible gel pack that is configured to contour to the user's body and transfer heat away (or to) the user's body. The pocket 200 may have a hemmed or sewn opening that stays open or may include one or more fasteners, e.g., a flap, buttons, etc., but it is preferred that the pocket 200 does not have any fasteners to provide comfort to the user and due to the heightened compression applied by the garment 100.

The front and/or rear abdominal portions 108, 110 also beneficially include a plurality of front or rear pressure protrusions 116a-n, 126a-n that provide pointed applied pressure to the targeted area of the user, particularly on or around the surgical area, wherein "n" represents any number greater than two. The plurality of front and rear pressure protrusions 116a-n, 126a-n are preferably and identically shaped, sized, and configured, but may be placed in different locations to target different areas on the user. Using the plurality of front pressure protrusions 116a-n as an example, each of the plurality of front pressure protrusions 116a-n project inwardly from the inner surface 114 of the front abdominal portion 108 wherein the at least one pocket 200 is located and extend toward the abdomen cavity 118 for application on the user. Each of the plurality of front and rear pressure protrusions 116a-n, 126a-n may span along the body length 600 beginning proximal to (e.g., at or near, within 15 cm) the respective upper terminal edges 300, 302 formed with the front and rear abdominal portions 108, 110. In some embodiments, the pressure protrusions 116a-n, 126a-n may span continuously from a point proximal to the upper terminal edges 300, 302 to a point proximal to the inseam. In preferred embodiments, however, the front pressure protrusions 116a-n extend continuously from a point proximal to the upper terminal edge 300 and to a point proximal to the inseam, wherein the front pressure protrusions 116a-n extend a width no greater than the front side-to-side width of the front abdominal portion 108. Preferably, the rear pressure protrusions 126a-n are formed in a rectangular array that extends continuously from a point proximal to the upper terminal edge 300 and to a point proximal to and aligned with the terminal edge 300 of the front abdominal portion 108. The width of the rear pressure protrusions 126a-n is preferably no greater than the rear side-to-side width of the rear abdominal portion 110.

The front or rear pressure protrusions 116a-n, 126a-n are preferably disposed in a tightly spaced configuration 800 with one another spanning along some portion of the body length 600. Preferably, the plurality of front and rear pressure protrusions 116a-n, 126a-n are disposed in the tightly spaced configuration 800 with one another, respectively, spanning at least 10% of the body length. In one embodiment, the tightly spaced configuration is no greater than approximately 8 mm (+/−4 mm) and is preferably no greater than 0.25 in. With reference to FIG. 1 and FIG. 8, each of the front or rear pressure protrusions 116a-n, 126a-n may also beneficially have a rounded tip, each have a width 802 ranging from approximately 1-2 mm (+/−0.5 mm), or 0.03-0.08 in., and a height 804 relative to the inner surface to which they are coupled ranging from approximately 0.2-0.5 mm (+/−0.1 mm), or 0.007-0.02 in. Preferably, however, the front or rear pressure protrusions 116a-n, 126a-n may have a width 802 of 1.425 mm and a height 804 of 0.325 mm. Because the garment 100 is designed to apply heightened compression, the rounded tip may be smooth and/or curvilinear.

In one embodiment, the rear abdominal portion 110 includes a single pocket that is preferably formed with the interior layer 122, wherein the interior layer 122 of the front abdominal portion 108 defines two pockets 200 flanking a slit 128 formed in the garment 100 and utilized to facilitate in placing the garment 100 on the user and removing the garment 100 from the user. The pocket(s) formed on the front and/or rear abdominal portions 108, 110 also beneficially include the plurality of front or rear pressure protrusions 116a-n, 126a-n directly coupled thereto, thereby enabling heat transfer to and from the targeted surgical area. Said another way, the interior layer 122 of the front abdominal portion 108 defines the at least one pocket 200 and includes the plurality of front pressure protrusions 116a-n directly coupled thereto. The plurality of front or rear pressure protrusions 116a-n, 126a-n may be directly coupled to the garment 100 using adhesive, welding, or other permanent or semi-permanent means.

In one embodiment, the plurality of front and rear pressure protrusions 116a-n, 126a-n are either of a glass-based material that may be formed into a composite material or a polymer-based material, such as a thermoplastic material, e.g., polylactic acid (PLA), a thermoplastic polyurethane (TPU) material, etc. The plurality of front and rear pressure protrusions 116a-n, 126a-n are preferably substantially rigid or non-elastic. In some embodiments, however, the plurality of front and rear pressure protrusions 116a-n, 126a-n are inherently elastic.

Further, in some embodiments the plurality of front and rear pressure protrusions 116a-n, 126a-n are of a thermally conductive material with thermal conductivity greater than 0.5 (W/m·K), i.e., Watts per meter per degree Kelvin. Preferably the thermal conductivity ranges from 0.5-50 (W/m·K), thereby enabling effective heat transfer between the targeted surgical area and the thermal pack(s) placed in the pocket(s). Some thermally conductive material examples include polyimide with 40% graphite, rubber filled with aluminum flakes, and other polymer materials using a high-aspect-ratio of conductive fillers like metalized glass and graphite fibers.

As seen in FIG. 1, the slit 128 defined by the unitary garment body 102, namely the front abdominal portion 108, may span continuously from the upper terminal edge 300 and may be selectively opened and closed through use of one or more fastener(s), e.g., hooks, clasps, Velcro, zipper assembly, etc. For some surgical operations, the slit 128 is not located centrally (geometrically) on the front abdominal portion 108, but is offset to the side (approximately 12 cm from the center) of the front abdominal portion 108, thereby providing only a single pocket on the front abdominal portion 108.

Although a specific order of steps associated with utilizing or assembly the garment 100 have been discussed or depicted, the order of executing the steps may be changed relative to the order shown in certain embodiments. Also, two or more steps described or shown as occurring in succession may be executed concurrently or with partial concurrence in some embodiments. Certain steps may also be omitted for the sake of brevity. In some embodiments, some or all of the process steps can be combined into a single process.

Further, various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A post-surgical compression garment comprising:
   a unitary garment body:
      defining two arm openings, two leg openings, an abdomen cavity, and a body length separating an upper terminal edge of the unitary garment body and a lower terminal edge of the unitary garment body;
      having a front abdominal portion interposed between the two arm openings and the two leg openings, of an elastic-based polymer material, with an outer surface, with an inner surface opposing the outer surface of the front abdominal portion, defining at least one pocket interposed between the outer and inner surfaces of the front abdominal portion and configured to enclose and define a pocket cavity shaped and sized to receive a thermal pack, and with a plurality of front pressure protrusions each projecting inwardly from the inner surface of the front abdominal portion having the at least one pocket and toward the abdomen cavity, disposed in a tightly spaced configuration with one another spanning along the body length, each having a rounded tip, and each having a width ranging from 1-2 mm and a height relative to the inner surface of the front abdominal portion ranging from 0.2-0.5 mm; and having a rear back portion opposing the front abdominal portion, interposed between the two arm openings and the two leg openings, of an elastic-based polymer material, with an outer surface, and with an inner surface opposing the outer surface of the rear abdominal portion.

2. The post-surgical compression garment according to claim 1, wherein the elastic-based polymer material of the front and rear abdominal portions is of a polyamide and elastane material.

3. The post-surgical compression garment according to claim 1, wherein the elastic-based polymer material of the front and rear abdominal portions is approximately 80% polyamide and approximately 20% elastane.

4. The post-surgical compression garment according to claim 1, wherein the front and rear abdominal portions each further comprise:

an interior layer of approximately 80% polyamide and 20% elastane and including the inner surface of the respective front abdominal portion or the rear abdominal portion; and an exterior layer coupled to the interior layer, of approximately 85% polyamide and 15% elastane, and including the outer surface of the respective front abdominal portion or the rear abdominal portion.

5. The post-surgical compression garment according to claim 4, wherein the interior layer of the front abdominal portion defines the at least one pocket and includes the plurality of front pressure protrusions directly coupled thereto.

6. The post-surgical compression garment according to claim 5, wherein the plurality of front pressure protrusions are either of a glass-based material or a polymer-based material.

7. The post-surgical compression garment according to claim 1, wherein the rear back portion further comprises:

at least one pocket defined thereon and interposed between the outer and inner surfaces of the rear abdominal portion and configured to enclose and define a pocket cavity shaped and sized to receive a thermal pack, and with a plurality of rear pressure protrusions each projecting inwardly from the inner surface of the rear abdominal portion having the at least one pocket and toward the abdomen cavity, disposed in a tightly spaced configuration with one another spanning along the body length, each having a rounded tip, and each having a width ranging from 1-2 mm and a height relative to the inner surface of the front abdominal portion ranging from 0.2-0.5 mm.

8. The post-surgical compression garment according to claim 7, wherein the front and rear abdominal portions each further comprise:

an interior layer of approximately 80% polyamide and 20% elastane and including the inner surface of the respective front or rear abdominal portion; and an exterior layer coupled to the interior layer, of approximately 85% polyamide and 15% elastane, and including the outer surface of the respective front or rear abdominal portion.

9. The post-surgical compression garment according to claim 8, wherein the interior layer of the front abdominal portion defines the at least one pocket and includes the plurality of front pressure protrusions directly coupled thereto and the interior layer of the rear abdominal portion defines the at least one pocket and includes the plurality of rear pressure protrusions directly coupled thereto.

10. The post-surgical compression garment according to claim 9, wherein the plurality of front pressure protrusions and the plurality of rear pressure protrusions are either of a glass-based material or a polymer-based material.

11. The post-surgical compression garment according to claim 10, wherein the plurality of front pressure protrusions and the plurality of rear pressure protrusions are of a thermally conductive material with a thermal conductivity greater than 0.5 (W/m·K).

12. The post-surgical compression garment according to claim 1, wherein the unitary garment body further comprises:

an upper terminal edge formed with the front abdominal portion;

a slit defined thereon and spanning from the upper terminal edge; and at least one fastener operably configured to open and close the slit.

13. The post-surgical compression garment according to claim 12, wherein the slit is centrally disposed on the front abdominal portion.

14. The post-surgical compression garment according to claim 12, wherein the plurality of front pressure protrusions span along the body length beginning proximal to the upper terminal edge formed with the front abdominal portion.

15. The post-surgical compression garment according to claim 1, wherein the plurality of front pressure protrusions are disposed in the tightly spaced configuration with one another spanning at least 10% of the body length.

16. The post-surgical compression garment according to claim 1, wherein the plurality of front pressure protrusions are disposed in the tightly spaced configuration no greater than approximately 8 mm.

17. A post-surgical compression garment comprising:
a unitary garment body:

defining two arm opening, two leg openings, an abdomen cavity, and a body length separating an upper terminal edge of the unitary garment body and a lower terminal edge of the unitary garment body;

having a front abdominal portion interposed between the two arm openings and the two leg openings, of an elastic-based polymer material, with an outer surface, with an inner surface opposing the outer surface of the front abdominal portion, defining at least one pocket interposed between the outer and inner surfaces of the front abdominal portion and configured to enclose and define a pocket cavity shaped and sized to receive a thermal pack, and with a plurality of front pressure protrusions each projecting inwardly from the inner surface of the front abdominal portion having the at least one pocket and toward the abdomen cavity, disposed in a tightly spaced configuration with one another spanning along the body length, each having a rounded tip; and having a rear back portion opposing the front abdominal portion, interposed between the two arm openings and the two leg openings, of an elastic-based polymer material, with an outer surface, with an inner surface opposing the outer surface of the rear abdominal portion, defining at least one pocket interposed between the outer and inner surfaces of the rear abdominal portion and configured to enclose and define a pocket cavity shaped and sized to receive a thermal pack, and with a plurality of rear pressure protrusions each projecting inwardly from the inner surface of the rear abdominal portion having the at least one pocket and toward the abdomen cavity, disposed in a tightly spaced configuration with one another spanning along the body length, and each having a rounded tip.

18. The post-surgical compression garment according to claim 17, wherein the plurality of front and rear pressure protrusions each comprise:

a width ranging from 1-2 mm and a height relative to the inner surface thereon ranging from 0.2-0.5 mm.

* * * * *